United States Patent [19]

Ciurca et al.

[11] B 3,998,640

[45] Dec. 21, 1976

[54] PHOTOGRAPHIC ELEMENTS CONTAINING N-OXIDE OXIDANTS

[75] Inventors: Samuel J. Ciurca; Albert T. Brault, both of Rochester, N.Y.

[73] Assignee: Eastman Kodak Company, Rochester, N.Y.

[22] Filed: June 5, 1973

[21] Appl. No.: 367,305

[44] Published under the second Trial Voluntary Protest Program on March 2, 1976 as document No. B 367,305.

[52] U.S. Cl. .......................................... 96/54; 96/3; 96/29 D; 96/55; 96/76 R; 96/77; 96/95; 96/119 R

[51] Int. Cl.$^2$ .................... G03C 7/00; G03C 5/54; G03C 1/48; G03C 1/06

[58] Field of Search ................. 96/76 R, 77, 119 R, 96/95, 3, 54, 29 D, 60 R, 55

[56] References Cited

UNITED STATES PATENTS

| | | | |
|---|---|---|---|
| 2,559,643 | 7/1951 | Land | 96/76 R |
| 2,661,293 | 12/1953 | Land | 96/76 R |
| 2,698,798 | 1/1955 | Land | 96/76 R |
| 2,892,710 | 6/1959 | Cohler et al. | 96/95 |
| 2,992,105 | 7/1961 | Corley et al. | 96/29 D |
| 3,065,074 | 11/1962 | Rogers | 96/29 D |
| 3,173,929 | 3/1965 | Kasman | 260/371 |
| 3,340,063 | 9/1967 | Kalenda | 96/95 |
| 3,384,484 | 5/1968 | Schranz et al. | 96/77 |
| 3,698,897 | 10/1972 | Gompf et al. | 96/77 |
| 3,709,690 | 1/1973 | Cohen et al. | 96/67 |

FOREIGN PATENTS OR APPLICATIONS

| | | |
|---|---|---|
| 2,126,954 | 12/1971 | Germany |
| 1,326,889 | 8/1973 | United Kingdom |

Primary Examiner—David Klein
Assistant Examiner—Richard L. Schilling
Attorney, Agent, or Firm—Ronald P. Hilst

[57] ABSTRACT

Heterocyclic N-oxides are useful as oxidants in photographic elements or film units.

18 Claims, No Drawings

PHOTOGRAPHIC ELEMENTS CONTAINING N-OXIDE OXIDANTS

FIELD OF THE INVENTION

This invention relates to the art of photography and particularly to photographic elements, such as color diffusion transfer elements, employing oxidizing agents.

BACKGROUND OF THE INVENTION

Color diffusion transfer processes generally involve the use of a photographic element comprising a support, at least one silver halide emulsion and an image dye-providing material which is contained in or contiguous said layer. After exposure, such a photographic element is treated with an alkaline processing solution to effect imagewise discrimination in the element. As is well known in the art, the dye-providing material can be initially immobile or initially mobile in the processing solution. Upon alkaline processing of an initially immobile dye-providing material, a mobile dye or dye precursor can be released imagewise or the material can be imagewise rendered soluble and thus mobile. If the material is initially mobile, the processing solution typically renders the material insoluble (and thus immobile) in an imagewise fashion. Whether initially mobile or immobile, upon treatment with a processing solution, the dye-providing material typically is oxidized under alkaline conditions thereby producing imagewise discrimination in the element.

Exemplary of such color diffusion transfer processes are those using developing agents as disclosed in U.S. Pat. Nos. 2,698,798 and 2,559,643 wherein a latent silver halide image is developed with a color developing agent. As development proceeds, the color developing agent reduces the exposed silver halide to metallic silver and the color developing agent which is oxidized as a function of development forms an immobile species while the unoxidized color developing agent is free to migrate to a receiving element. After migration, the color developing agent in the receiver is oxidized. The oxidized developing agent then self-couples or couples with a color coupler to form a positive dye image.

A more recent example of a photographic process in which oxidation causes formation of an image dye is described in copending Lestina and Bush U.S. Pat. application Ser. No. 308,869, filed Nov. 22, 1972, and entitled PHOTOGRAPHIC ELEMENTS CONTAINING OXICHROMIC COMPOUNDS. Those oxichromic compounds are ones which undergo chromogenic oxidation to form a new chromophore. Useful materials of that type are oxichromic compounds which contain a developing moiety and an oxichromic moiety and have the general formula D-(OC) wherein D is a group which is a silver halide developer such as a hydroquinone moiety and OC is a moiety which undergoes chromogenic oxidation to form an image dye. These oxichromic compounds are particularly useful in an image transfer unit format in which the respective initially diffusible oxichromic compounds or the initially nondiffusible compounds are used in combination with the appropriate silver halide emulsions.

In order to achieve optimum results when using such oxichromic compounds, it is desirable to have an oxidant which can be easily incorporated in a photographic element with good stability and which will readily oxidize the oxichromic moiety without adversely affecting other ingredients of a given photographic element or film unit. The oxidative conversion of oxichromic compounds or of other color-providing materials is necessary in order to achieve color image formation. Accordingly, there is a continuing need in the art for materials which exhibit suitable oxidation capability.

SUMMARY OF THE INVENTION

We have found a class of oxidants well suited for use in color diffusion transfer color elements and in any other photographic element in which an oxidant is a necessary or desirable ingredient. When used in photographic elements containing certain oxichromic compounds, the oxidant readily oxidizes the oxichromic moiety.

DESCRIPTION OF PREFERRED EMBODIMENTS

The objects of the present invention are achieved through the use in photographic element, e.g., a color diffusion transfer element, of a class of heterocyclic N-oxides. Typically, these compounds are used in a photosensitive element comprising a support having thereon at least one photographic image recording layer, and at least one layer having associated therewith a heterocyclic N-oxide of this invention.

The heterocyclic N-oxides useful in this invention include those represented by the formula:

1. 

wherein:

Z represents the nonmetallic atoms necessary to complete a 5- or 6-membered aromatic heterocyclic nucleus having up to three hetero atoms, such as nitrogen and oxygen. The 5- or 6-membered heterocyclic nucleus can be substituted with a wide variety of substituents. Additionally, the heterocyclic nucleus can have saturated or unsaturated ring structures fused thereto. Useful N-oxides include those wherein Z represents the nonmetallic atoms necessary to complete an oxadiazole nucleus or a pyridine nucleus.

The heterocyclic N-oxides which give particularly good results in the practice of this invention can be characterized in terms of their polarographic halfwave potentials, i.e., their oxidation or reduction potentials as determined by polarography. Cathodic measurements of the reduction potential can be made with a solution of N-oxide, typically in a basic solvent such as potassium hydroxide, using a dropping mercury electrode with the polarographic halfwave potential for the most positive wave being designated $E_c$. In each measurement, the reference electrode is a standard Calomel electrode. Electrochemical measurements of this type are known in the art and are described in *New Instrumental Methods in Electrochemistry*, by Delahay, Interscience Publishers, New York, New York, 1954; *Polarography*, by Kolthoff and Lingane, 2nd Ed., Interscience Publishers, New York, N.Y., 1952; *Analytical Chemistry*, 36, 2426 (1964) by Elving; and *Analytical Chemistry*, 30, 1576 (1958) by Adams. Plus and minus signs are according to IUPAC (International Union of Pure and Applied Chemistry) Stockholm Convention 1953. Useful N-oxides should have a polarographic reduction potential which is more positive than the polarographic oxidation potential of the ingredients to be oxidized. In general, useful N-oxides include those having a polarographic reduction potential more positive than about −0.5 v. Typical N-oxides for use in oxichromic processes, as described by Lestina and Bush in U.S. Pat. Application Ser. No. 308,869 mentioned above, are those having a reduction potential, $E_c$, between about −0.1 and −0.5 v.

Preferred N-oxides are benzofuroxans and 4,4'-azopyridine-1,1'-dioxides having the formulas II and III, respectively:

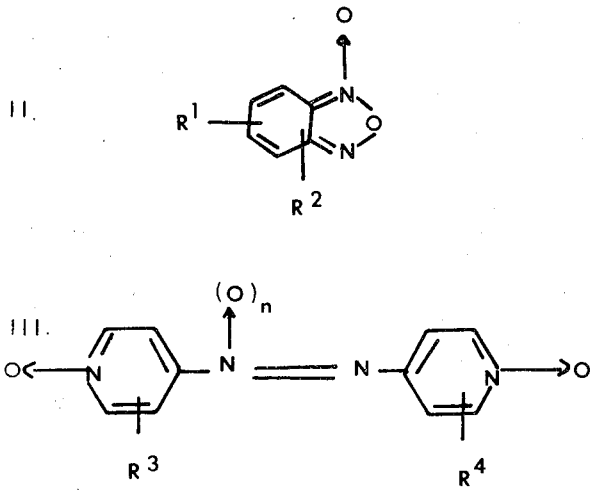

wherein:

$R^1$ and $R^2$ each represent a hydrogen atom, an alkyl group having 1 to about 25 carbon atoms, an alkoxy group having 1 to about 25 carbon atoms, a halogen atom, a nitro group, an oxo-linked benzofuroxan or an organic ballasting group of such size and configuration (e.g., simple organic groups or polymeric groups) as to render the compound nondiffusible, especially during treatment with an alkaline processing composition;

$n$ is an integer having a value of 0 or 1; and $R^3$ and $R^4$ each represent a hydrogen atom, an alkyl group having 1 to about 25 carbon atoms, an alkoxy group having 1 to about 25 carbon atoms, or an organic ballasting group as described above for $R^1$ and $R^2$. Suitable ballasting groups typically contain an alkyl group (branched or unbranched), an aryl group, an aralkyl group or an alkaryl group and typically contain from about 8 to 25 carbon atoms.

A further discussion of useful heterocyclic N-oxides and methods for their preparation can be found in Chemistry of the Heterocyclic N-Oxides, A. R. Katritzky and J. M. Yagowski (1971) incorporated herein by reference. The 4,4'-azopyridine-1,1'-dioxides can be prepared as described by E. L. Eichhorn in Acta. Cryst., 1959, Vol. 12, p. 746, incorporated herein by reference. The benzofuroxans can be prepared by the pyrolysis of o-nitrophenyl azides and by the oxidation of o-nitroanilines as described by Katritzky et al (supra), p. 733 et. seq.

The heterocyclic N-oxides described herein can be used in a wide variety of photographic elements or in photographic film units.

In certain embodiments, the N-oxides can be used in photographic elements or film units to provide an oxidant for the synthesis of image dyes. The heterocyclic N-oxides can be used to generate oxidized color developing agent which then reacts with a color coupler to form the image dye. Additionally, these radicals can be used to oxidize a compound directly to an image dye as in the case of leuco indoanilines, leuco indophenols, leuco triarylmethanes and other dye precursors.

In one embodiment, the present N-oxides are useful in color diffusion transfer processes such as those in which unreacted color formers in undeveloped or partially developed areas of a photographic element diffuse imagewise, after color development of the exposed layers, to a receiving layer in which the color formers react with oxidized color developer to produce an imagewise distribution of dye. By including a useful N-oxide in the receiving layer or having it in association therewith, dyes are formed imagewise in that element as a result of the interreaction of the oxidant, color developer and diffused color former. Processes of this type are described further in British Pat. No. 926,462, dated May 15, 1963, incorporated herein by reference.

Examples of processes in which an image is formed upon oxidation of transferred color developer and color coupler are described in U.S. Pat. Nos. 2,559,293 and 2,698,798, incorporated herein by reference. Similarly, the present oxidants can be used in imaging processes based on leuco anthraquinones and other dye precursors which produce dyes when oxidized or processes based on developers which self-couple upon oxidation, thereby producing dyes. Processes of these latter types are described further in U.S. Pat. Nos. 2,892,710 and 2,698,798, respectively, both incorporated herein by reference. Likewise, the described heterocyclic N-oxides have utility in color diffusion transfer processes using a leuco developing agent, as discussed in U.S. Pat. Nos. 2,992,105 and 2,909,430, incorporated herein by reference.

In another embodiment, the described N-oxides can be used to oxidize the developer portion of a dye developer (i.e., a compound which contains a silver halide developing moiety and a separate moiety which contains the chromophore of an image dye). As mentioned above, the N-oxide selected must have an oxidation potential sufficient to oxidize the developer portion of the molecule, such as the hydroquinone portion. In this embodiment, the oxidant can function to immobilize the dye developer, such as when it diffuses to the receiver layer, by forming the quinone, quinonimide, etc, of the developer moiety which is generally quite insoluble in an alkaline processing solution.

In other embodiments, the heterocyclic N-oxides can be used to stabilize a preformed image dye. In some embodiments, the N-oxides produce a beneficial increase in the stability of azo dyes which are transferred to an image-receiving layer.

In still other embodiments, a photographic element containing an N-oxide oxidant can be treated to form an imagewise distribution of the oxidant. The photographic element can then be contacted with a material which will undergo oxidation to produce an image record in the photographic element. Also, the photographic element containing the imagewise distribution of oxidant can be treated to effect diffusion of the oxidant to an adjacent layer wherein it can oxidize materials to produce an image record. In one example of this embodiment, a photographic element containing a silver halide emulsion and an adjacent layer containing a nondiffusible N-oxide oxidant can be developed with a silver halide developer. Where silver halide is not developed, the oxidant will be reduced. The element can then be contacted with a solution of color coupler and color developer to react with the remaining imagewise distribution of the described N-oxide and produce an image dye.

The heterocyclic N-oxides of this invention are particularly well suited for use as oxidants in photographic elements or film units which contain an oxichromic compound of the type described in copending Lestina and Bush U.S. Pat. application Ser. No. 308,869, mentioned above and incorporated herein by reference. Preferred oxichromic compounds are those which undergo chromogeneic oxidation to form a photographic image dye. In one embodiment, the N-oxide oxidant incorporated into photographic elements containing oxichromic compounds of the formula:

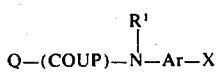

wherein (COUP) is a photographic color coupler linked to the nitrogen atom through a carbon atom at the coupling position, such as a phenolic coupler, a pyrazolone coupler, a pyrazolotriazole coupler, couplers having open-chain ketomethylene groups and the like; Ar is an arylene group containing from 6 to 20 carbon atoms, including substituted and unsubstituted arylene groups, fused-ring arylene groups and the like; X can be an amino group, including substituted amines, a hydroxyl group or the group:

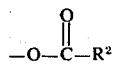

in which $R^2$ is a group containing from 1 to 12 carbon atoms, which can be an alkyl group, an aryl group, including a substituted alkyl group, a substituted aryl group and the like; $R^1$ is a hydrogen atom or the group:

in which $R^2$ is as defined above and is preferably a polyhalogenated alkyl group; and Q is a group which is (1) a silver halide developing agent which is preferably an aromatic group polysubstituted with hydroxy, amino or substituted amino groups or (2) an oxidizable releasing group (i.e., a group which can be oxidized to facilitate subsequent release of a group or a group which can be oxidized to prevent the normal release of a group under the processing conditions). When Q is a silver halide developing agent, the resultant compound preferably is initially mobile. When Q is an oxidizable releasing group, the resultant compound preferably is initially immobile.

Typically, the present oxidants are used in either the processing fluid or the image receiving layer of a diffusion transfer film unit employing other image dye-providing materials mentioned above. The image-transfer film units can be any of those described in the following patents, all incorporated herein by reference: U.S. Pat. Nos. 2,543,181, 2,983,606, 3,227,550, 3,227,552, 3,415,644, 3,415,645, 3,415,646 and 3,635,707, Canadian Pat. No. 674,082, and Belgian Pat. Nos. 757,959 and 757,960, both issued Apr. 23, 1971.

When used in the processing fluid of various color diffusion transfer film units, the heterocyclic N-oxide is typically present in solution in a concentration of about 0.01 to about 0.1 molar. When not contained in the processing fluid, the present N-oxide oxidants are coated in at least one layer which typically contains a binder such as gelatin, poly(vinyl alcohol), etc. Of course, the heterocyclic N-oxides described herein can also be one of several ingredients as a given layer. For example, when used in color diffusion transfer units, the described oxidant can be contained in a mordant layer. In general, these N-oxides are coated at a coverage of about 40 to 500 mg/ft$^2$. In preferred embodiments, the heterocyclic N-oxides are used in image-transfer film units which are designed to be processed with a single processing solution, and the resulting positive image is viewed through a transparent support against an opaque background, preferably where all of the silver halide recording layers and the image-receiving layer remain laminated between two dimensionally stable supports after processing.

A suitable image transfer film unit in which the present oxidants are useful typically comprises:

1. a photosensitive element comprising a support having thereon at least one layer containing a silver halide emulsion having associated therewith an image dye-providing material and preferably at least three of said layers wherein one layer contains a blue-sensitive silver halide emulsion, one layer contains a green-sensitive silver halide emulsion, and one layer contains a red-sensitive silver halide emulsion;

2. an image-receiving layer which can be located on a separate support superposed or adapted to be superposed on said photosensitive element or, preferably, it can be positioned in the photosensitive element on the same support adjacent to the photosensitive silver halide emulsion layers; and 3. means containing an alkaline processing composition adapted to discharge its contents within said film unit. Where the receiver layer is coated on the same support with the photosensitive silver halide layers, the support is preferably a transparent support, an opaque layer is preferably positioned between the image-receiving layer and the photosensitive silver halide layer, and the alkaline processing composition preferably contains an opacifying substance such as carbon or pH-indicator dye which is discharged into the film unit between a dimensionally stable support or cover sheet and the photosensitive element. In certain embodiments, the cover sheet can be superposed or adapted to be superposed on the photosensitive element. The image-receiving layer can be coated on the cover sheet. In certain preferred embodiments where the image-receiving layer is located in the photosensitive element, a neutralizing layer is located on the cover sheet.

The means for containing the alkaline processing solution can be any means known in the art for this purpose, including rupturable containers positioned at the point of desired discharge of its contents into the film unit and adapted to be passed between a pair of juxtaposed rollers to effect discharge of the contents into the film unit, frangible containers positioned over or within the photosensitive element, hypodermic syringes, and the like.

The silver halide emulsions useful in our invention are well known to those skilled in the art and are described in *Product Licensing Index*, Vol. 92, Dec. 1971, publication 9232, p. 107, paragraph I, "Emulsion types;" they may be chemically and spectrally sensitized as described on page 107, paragraph III, "Chemical sensitization," and pp. 108–109, paragraph XV, "Spectral sensitization," of the above article; they can be protected against the production of fog and can be stabilized against loss of sensitivity during keeping by employing the materials described on p. 107, paragraph V, "Antifoggants and stabilizers," of the above article; they can contain development modifiers, hardeners, and coating aids as described on pp. 107–108, paragraph IV, "Development modifiers," paragraph VII, "Hardeners;" and paragraph XII, "Coating aids," of the above article; they and other layers in the photographic elements used in this invention can contain plasticizers, vehicles and filter dyes described on p. 108, paragraph XI, "Plasticizers and lubricants," and paragraph VIII, "Vehicles," and p. 109, paragraph XVI, "Absorbing and filter dyes," of the above article; they and other layers in the photographic elements used in this invention may contain addenda which are incorporated by using the procedures described on p. 109, paragraph XVII, "Methods of addition," of the above article; and they can be coated by using the various techniques described on p. 109, paragraph XVIII, "Coating procedures," of the above article, the disclosures of which are hereby incorporated by reference.

Any material can be employed as the image-receiving layer in this invention as long as the desired function of mordanting or otherwise fixing the dye images will be obtained. The particular material chosen will, of course, depend upon the dye to be mordanted. If acid dyes are to be mordanted, the image-receiving layer can contain basic polymeric mordants such as polymers of amino guanidine derivatives of vinyl methyl ketone such as described in Minsk U.S. Pat. No. 2,882,156, issued Apr. 14, 1959, and basic polymeric mordants such as described in Cohen et al U.S. Pat. No. 3,709,690, issued Jan. 9, 1973.

Additional mordants include cationic mordants such as polymeric compounds composed of a polymer having quaternary nitrogen groups and at least two aromatic nuclei for each quaternary nitrogen in the polymer cation (i.e., having at least two aromatic nuclei for each positively charged nitrogen atom), such polymeric compounds being substantially free of carboxy groups. Useful mordants of this type are comprised of units of the following formula in copolymerized relationship with units of at least one other ethylenically unsaturated monomer:

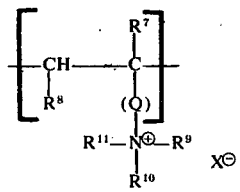

wherein $R^7$ and $R^8$ each represent a hydrogen atom or a lower alkyl radical (of 1 to about 6 carbon atoms) and $R^8$ can additionally be a group containing at least one aromatic nucleus (e.g., phenyl, naphthyl, tolyl); Q can be a divalent alkylene radical (of 1 to about 6 carbon atoms), a divalent arylene radical, a divalent aralkylene radical, a divalent arylenealkylene radical,

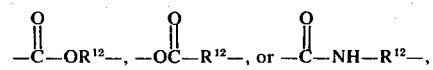

wherein $R^{12}$ is an alkylene radical, or $R^8$ can be taken together with Q to form a

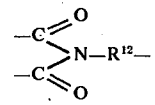

group; $R^9$, $R^{10}$ and $R^{11}$ can be lower alkyl or aryl, or $R^9$ and $R^{10}$ and the nitrogen atom to which they are attached can together with Q represent the atoms and bonds necessary to form a quaternized nitrogen-containing heterocyclic ring, and $X^-$ is monovalent negative salt forming radical or atom in ionic relationship with the positive salt forming radical; wherein said polymer is substantially free of carboxy groups and wherein the positive salt forming radical of said polymer comprises at least two aryl groups for each quaternary nitrogen atom in said polymer. These preferred polymeric cationic mordants are described further in the above-mentioned U.S. Pat. No. 3,709,690.

Other mordants useful in our invention include poly-4-vinylpyridine, the 2-vinylpyridine polymer metho-p-toluene sulfonate and similar compounds described in Sprague et al U.S. Pat. NO. 2,484,430, issued Oct. 11, 1949, and cetyl trimethylammonium bromide, etc. Effective mordanting compositions are also described in Whitmore U.S. Pat. NO. 3,271,148 and Bush U.S. Pat. No. 3,271,147, both issued Sept. 6, 1966.

The following examples are included for a further understanding of the present invention. In these examples, all temperatures indicated are Centigrade. All oxidants referred to are found in Table I below. The structural formulas for other compounds used are found in the footnotes to the examples. Examples 3, 4, 5, and 6 describe representative techniques used in the preparation of heterocyclic N-oxides of this invention.

EXAMPLE 1

The oxidants listed in Table I below are tested as follows: A matrix element prepared comprising a transparent film base support having a layer of 125 mg/ft$^2$ gelatin and 50 mg/ft$^2$ of oxichromic compound dissolved in 75 mg/ft$^2$ of diethyl lauramide. A receiver element is prepared comprising a transparent film base support having on it a first layer of 200 mg/ft$^2$ of the mordant copoly[styrene:N,N-dimethyl-N-benzyl-N-3-maleiimidopropyl)ammonium chloride] in 100 mg/ft$^2$ of gelatin and a second layer (over the first layer) comprising 2000 mg/ft$^2$ of titanium dioxide in 200 mg/ft$^2$ of gelatin. The two elements are then placed in face-to-face contact for 60 seconds with an alkaline processing composition, comprising 20 g. of oxidant per liter of an aqueous solution of 4% potassium hydroxide and 2.5% hydroxyethylcellulose, spread between the elements. Upon contact of the two elements, the oxichromic compound migrates from the matrix through the processing composition and the titanium dioxide layer into the mordant layer of the receiver. The oxichromic compound is oxidized by the N-oxide oxidant to the corresponding dye which is visible through the transparent support and against the white background of the titanium dioxide layer. The oxichromic compounds and the oxidants used as well as the color and reflection density of the dye in the receiver are shown in Table I below.

Table I

| Oxidant No.** | Oxichromic Compound* | Color of Dye in Receiver | $D_{max}$ |
|---|---|---|---|
| 1 | A | Yellow | 1.7 |
| 1 | B | Magenta | 1.5 |
| 1 | C | Cyan | 1.7 |
| 2 | A | Yellow | 1.7 |
| 2 | B | Magenta | 1.0 |
| 2 | C | Cyan | 1.2 |
| 3 | A | Yellow | 2 |
| 3 | B | Magenta | 1.5 |
| 3 | C | Cyan | 1.8 |
| 4 | B | Magenta | 1.5 |
| 5 | A | Yellow | 0.8 |
| 5 | B | Magenta | 2.4 |
| 6 | B | Magenta | 1.2 |
| 6 | C | Cyan | 1.0 |

*Oxichromic Compound:

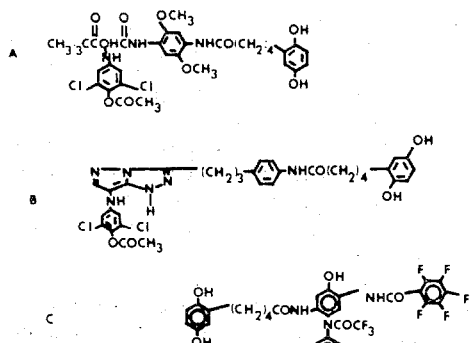

**Oxidants

Oxidant No. 1
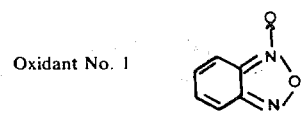

Oxidant No. 2
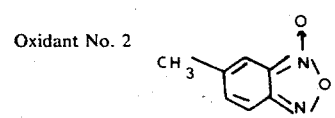

Oxidant No. 3
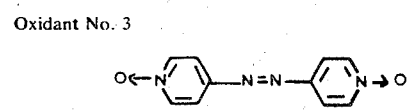

Oxidant No. 4
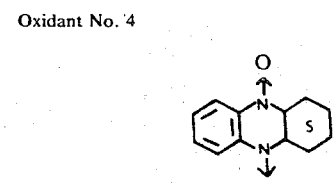

Table I-continued

| Oxidant No.** | Oxichromic Compound* | Color of Dye in Receiver | $D_{max}$ |
|---|---|---|---|

Oxidant No. 5
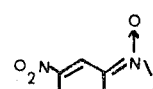

Oxidant No. 6
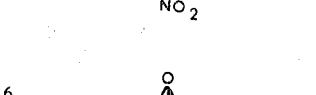

EXAMPLE 2

An integral, color transfer, photographic element is prepared having the following structure:
1. transparent polyethylene terephthalate support;
2. dye mordant layer containing gelatin at 100 mg/ft², copoly[styrene:N-benzyl-N,N-dimethyl-N-(3-maleimidopropyl)ammonium chloride] at 200 mg/ft² and N-oxide oxidant No. 1 at 200 mg/ft²;
3. layer containing titanium dioxide at 2000 mg/ft² and gelatin at 200 mg/ft²;
4. layer containing carbon opacifying agent at 200 mg/ft² and gelatin at 156 mg/ft²;
5. layer containing gelatin at 75 mg/ft², 2,5-disec-dodecylhydroquinone at 70 mg/ft² and tricresyl phosphate at 23 mg/ft².
6. layer containing a red-sensitive silver bromoiodide emulsion at 70 mg/ft² based on silver, gelatin at 230 mg/ft², Compound D** at 42 mg/ft² dispersed in diethyl lauramide at 73 mg/ft², 5-(2-cyanoethylthio)-1-phenyltetrazole at 5 mg/ft² dispersed in tricresyl phosphate at 15 mg/ft² and 5,6,7,8-tetrahydro-5,8-methano-1,4-naphthalenediol at 10 mg/ft²;

**Compound D

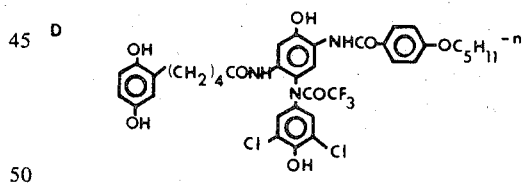

7. layer containing gelatin at 300 mg/ft², 2,5-disec-dodecylhydroquinone at 70 mg/ft² and a magenta filter dye at 30 mg/ft² dissolved in diethyl lauramide at 50 mg/ft²;
8. layer containing green-sensitive silver bromoiodide emulsion at 70 mg/ft² based on silver, gelatin at 230 mg/ft², oxichromic compound B at 54 mg/ft² dispersed in diethyl lauramide at 64 mg/ft², 5-(2-cyanoethylthio)-1-phenyltetrazole at 5 mg/ft² dispersed in tricresyl phosphate and 5,6,7,8-tetrahydro-5,8-methano, 1,4-naphthalenediol at 10 mg/ft²;
9. layer containing gelatin at 300 mg/ft², 2,5-disec-dodecylhydroquinone at 70 mg/ft² and a yellow filter dye at 100 mg/ft² dispersed in diethyl lauramide at 28 mg/ft²;
10. layer containing a blue-sensitive silver bromoiodide emulsion at 70 mg/ft² based on silver, gelatin at 210 mg/ft², oxichromic compound A at 64 mg/ft² dispersed in diethyl lauramide at 106 mg/ft², 5-(2-cyanoethylthio)-1-phenyltetrazole at 5 mg/ft² dispersed in tricresyl phosphate at 15 mg/ft² and 5,6,7,8-tetrahydro-5,8-methano-1,4-naphthalenediol at 10 mg/ft²;

11. layer containing gelatin at 50 mg/ft².

A transparent cover sheet for the above element is prepared as follows:
1. transparent polyethylene terephthalate support;
2. layer containing gelatin at 900 mg/ft², polyacrylic acid at 900 mg/ft² and imidazole at 760 mg/ft²;
3. layer containing cellulose acetate at 1140 mg/ft² and copoly(styrene-maleic anhydride) at 60 mg/ft².

The photographic element is exposed through a multi-color, graduated-density test object, the transparent cover sheet superposed on the element, and a pod containing a opaque processing composition is ruptured to discharge between the cover sheet and the photosensitive element by passing the film unit through juxtaposed rollers having a gap of about 8 mils. The processing composition is as follows:

| | |
|---|---|
| potassium hydroxide | 51 g/l |
| hydroxyethyl cellulose | 30 g/l |
| potassium bromide | 40 g/l |
| α-benzylpicolinium bromide | 15 g/l |
| 5,6,7,8-tetrahydro-5,8-methano-1,4-naphthalenediol | 15 g/l |
| carbon | 40 g/l |

After about 1 to 2 minutes, a well-defined color image with excellent color reproductin is viewed through the transparent support of the integral element.

Examples 3 and 4 are included to demonstrate representative preparation for the N-oxide compounds used in this invention.

EXAMPLE 3

Preparation of Compound No. 2

Twenty-one grams (0.32 mole) of potassium hydroxide are dissolved in 300 ml. of 95% ethanol. Upon the addition of 44 g. (0.29 mole) of 4-methyl-2-nitroaniline, with stirring, the mixture is cooled to 0°C using a dry ice/acetone bath. A 715 g. portion of a 6% aqueous sodium hypochlorite solution cooled to 0°C is added to the above mixture over a period of about 30 minutes. After continued stirring for about one-half hour, a yellow solid is collected on a Buchner funnel, washed with water, and without drying, recrystallized from ethanol. The melting point of the product is 94°–96°C.

EXAMPLE 4

Preparation of compound No. 4

A quantity of 13.6 g. (0.1 mole) of benzofuroxan is dissolved in 200 ml. of warm methanol. Then, 16.7 g. (0.1 mole) of 1-morpholino-1-cyclohexene is slowly added. The mixture is stirred for about one-half hour and concentrated to one-half its original volume. The obtained solid is collected on a Buchner funnel, then recrystallized from methanol. The product consists of 3.1 g. of a yellow crystalline solid, mp 195°–197° dec.

The term "image dye-providing material" as used herein is understood to refer to those compounds which either (1) do not require a chemical reaction to form the image dye or (2) undergo reactions encountered in photographic imaging systems to produce an image dye, such as with color couplers, oxichromic compounds and the like. The first class of compounds is generally referred to as preformed image dyes and includes shifted dyes, etc, while the second class of compounds is generally referred to as dye precursors.

The terms "initially mobile" and "initially immobile" as used herein refer to compounds which are incorporated in the photographic element and, upon contact with an alkaline processing solution, are substantially mobile or substantially immobile, respectively.

The invention has been described in detail with particular reference to certain preferred embodiments thereof, but it will be understood that variations and modifications can be effected within the spirit and scope of the invention.

We claim:

1. A photographic element comprising a support having thereon at least one photographic dye-image receiving layer and at least one layer containing at least 40 mg per ft² of an aromatic heterocyclic N-oxide oxidant having a polarographic reduction potential more positive than about −0.5 v when in an aqueous solution comprising 4% potassium hydroxide.

2. In a photographic element containing an image dye-providing material which is oxidized under alkaline conditions to form an image dye and at least one photographic dye-image receiving layer, the improvement wherein said element also comprises at least 40 mg per ft² of an aromatic heterocyclic N-oxide oxidant having a polarographic reduction potential of between about −0.1 and −0.5 v when in an aqueous solution comprising 4% potassium hydroxide.

3. A photographic element comprising a support having thereon at least one photosensitive silver halide emulsion layer and at least one layer containing at least 40 mg per ft² of a compound of the formula:

wherein Z represents the nonmetallic atoms necessary to complete a 5- or 6-membered heterocyclic nucleus having up to three hetero atoms.

4. A photographic element as described in claim 3 wherein Z represents the atoms necessary to complete a pyridine nucleus.

5. A photographic element as described in claim 3 wherein Z represents the atoms necessary to complete an oxadiazole nucleus.

6. A photographic film unit comprising
a. a photosensitive element comprising a support having thereon a photosensitive silver halide emulsion having associated therewith an image dye-providing compound;
b. a dye image-receiving layer; and
c. means for discharging an alkaline processing composition contained within said film unit; said film unit containing an aromatic heterocyclic N-oxide oxidant for said dye-providing compound, and said N-oxide having a polarographic reduction potential more positive than about −0.5 v when in an aqueous solution comprising 4% potassium hydroxide.

7. The film unit as described in claim 6 wherein said N-oxide is contained in said alkaline processing composition.

8. The film unit as described in claim 6 wherein said N-oxide is associated with said image receiving layer.

9. The film unit as described in claim 6 wherein said N-oxide is a benzofuroxan.

10. The film unit as described in claim 6 wherein said N-oxide is a 4,4'-azopyridine-1,1'-dioxide.

11. A photographic film unit comprising:
a. a photosensitive element comprising a support having thereon a layer containing a red-sensitive silver halide emulsion having associated therewith a cyan image dye-providing material, a layer containing a green-sensitive silver halide emulsion having associated therewith a magenta image dye-providing material, and a layer containing a blue-sensitive silver halide emulsion having associated therewith a yellow image dye-providing material,
b. an image dye-receiving layer; and
c. means for discharging an alkaline processing composition within said film unit;
said film unit containing an aromatic heterocyclic N-oxide selected from the group consisting of a benzofuroxan and a 4,4'-azopyridine-1,1'-dioxide.

12. A film unit as described in claim 11 wherein at least one of said image dye-providing materials is an oxichromic compound.

13. A film unit as described in claim 11 wherein at least one of said image dye-providing materials is an oxichromic compound having the formula:

$$Q-(COUP)-\underset{\underset{R^1}{|}}{N}-Ar-X$$

wherein:
(COUP) is a photographic color coupler linked to the nitrogen atom through a carbon atom at the coupling position;
Ar is an arylene group;
X is selected from an amino group, a hydroxyl group or a group having the formula:

$$-O-\underset{\underset{}{\overset{\overset{O}{\|}}{C}}}-R^2$$

wherein $R^2$ is an alkyl or aryl group;
$R^1$ is a hydrogen atom or a group having the formula:

$$-\underset{}{\overset{\overset{O}{\|}}{C}}-R^2$$

wherein $R^2$ is as defined above; and
Q is a silver halide developing agent or an oxidizable releasing group.

14. In a photographic process wherein an exposed photographic silver halide emulsion is developed and wherein an image dye-providing material is oxidized to provide an image dye record, the improvement comprising oxidizing said material with an aromatic heterocyclic N-oxide having a polarographic reduction potential more positive than about −0.5 v when in an aqueous solution comprising 4% potassium hydroxide.

15. A photographic element comprising a support having thereon at least one photographic silver halide emulsion layer and at least 40 mg per ft² of an aromatic heterocyclic N-oxide oxidant having a polarographic reduction potential more positive than about −0.5 v when in an aqueous solution comprising 4% potassium hydroxide.

16. A photographic element comprising a support having thereon at least one photographic dye-image receiving layer and at least one layer containing at least 40 mg per ft² of a compound having a formula selected from

[benzofuroxan structure with $R^1$ and $R^2$ substituents]

and

[4,4'-azopyridine dioxide structure with $R^3$, $R^4$ substituents and $(O)_n$]

wherein:
$R^1$ and $R^2$ each represents a hydrogen atom, an alkyl group having from 1 to 7 carbon atoms, an alkoxy group having from 1 to about 25 carbon atoms, a halogen atom, a nitro group, an oxo-linked benzofuran or an organic ballasting group having from about 8 to about 25 carbon atoms and comprising an alkyl group, an aryl group, an aralkyl group or an alkaryl group,
$n$ is an integer having a value of 0 or 1, and
$R^3$ and $R^4$ each represents a hydrogen atom, an alkyl group having from 1 to 7 carbon atoms, an alkoxy group having from 1 to about 25 carbon atoms or an organic ballasting group having from about 8 to about 25 carbon atoms and comprising an alkyl group, an aryl group, an aralkyl group or an alkaryl group.

17. In a photographic element containing an image dye-providing material which is oxidized under alkaline conditions to form an image dye and at least one photographic dye-image receiving layer, the improvement wherein said element also comprises at least 40 mg per ft² of a compound having a formula selected from

[benzofuroxan structure with $R^1$ and $R^2$ substituents]

and

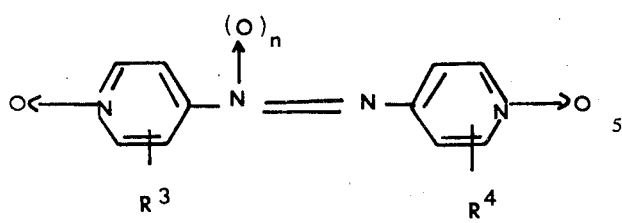

wherein:
R¹ and R² each represents a hydrogen atom, an alkyl group having from 1 to 7 carbon atoms, an alkoxy group having from 1 to about 25 carbon atoms, a halogen atom, a nitro group, an oxo-linked benzofuran or an organic ballasting group having from about 8 to about 25 carbon atoms and comprising an alkyl group, an aryl group, an aralkyl group or an alkaryl group, $n$ is an integer having a value of 0 or 1, and R³ and R⁴ each represents a hydrogen atom, an alkyl group having from 1 to 7 carbon atoms, an alkoxy group having from 1 to about 25 carbon atoms or an organic ballasting group having from about 8 to about 25 carbon atoms and comprising an alkyl group, an aryl group, an aralkyl group or an alkaryl group.

18. A photographic element comprising a support having thereon at least one photosensitive silver halide emulsion layer and at least one layer containing at least 40 mg per ft² of a compound having a formula selected from

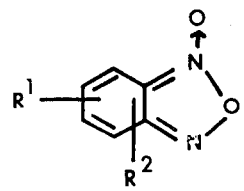

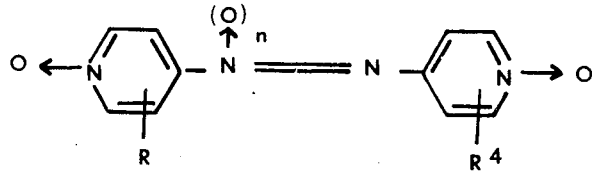

wherein:
R¹ and R² each represents a hydrogen atom, an alkyl group having from 1 to 7 carbon atoms, an alkoxy group having from 1 to about 25 carbon atoms, a halogen atom, a nitro group, an oxo-linked benzofuran or an organic ballasting group having from about 8 to about 25 carbon atoms and comprising an alkyl group, an aryl group, an aralkyl group or an alkaryl group, $n$ is an integer having a value of 0 or 1, and R³ and R⁴ each represents a hydrogen atom, an alkyl group having from 1 to 7 carbon atoms, an alkoxy group having from 1 to about 25 carbon atoms or an organic ballasting group having from about 8 to about 25 carbon atoms and comprising an alkyl group, an aryl group, an aralkyl group or an alkaryl group.

* * * * *